US010755187B2

(12) United States Patent
Egi et al.

(10) Patent No.: US 10,755,187 B2
(45) Date of Patent: Aug. 25, 2020

(54) MOOD SCORE CALCULATION SYSTEM

(71) Applicant: Hitachi, Ltd., Tokyo (JP)

(72) Inventors: Masashi Egi, Tokyo (JP); Masashi Kiguchi, Tokyo (JP); Hirokazu Atsumori, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 703 days.

(21) Appl. No.: 15/532,434

(22) PCT Filed: Jun. 17, 2015

(86) PCT No.: PCT/JP2015/067465
§ 371 (c)(1),
(2) Date: Jun. 1, 2017

(87) PCT Pub. No.: WO2016/203575
PCT Pub. Date: Dec. 22, 2016

(65) Prior Publication Data
US 2017/0270423 A1 Sep. 21, 2017

(51) Int. Cl.
G06N 7/00 (2006.01)
G06Q 10/10 (2012.01)
G16H 50/30 (2018.01)
G06Q 10/06 (2012.01)

(52) U.S. Cl.
CPC .......... *G06N 7/005* (2013.01); *G06Q 10/105* (2013.01); *G06Q 10/063114* (2013.01); *G16H 50/30* (2018.01)

(58) Field of Classification Search
CPC .............. G06N 7/005; G06Q 10/105; G06Q 10/063114; G16H 50/30
See application file for complete search history.

(56) References Cited

U.S. PATENT DOCUMENTS 9,208,053 B2 * 12/2015 Kejariwal ........... G06F 11/3419
2012/0004511 A1 * 1/2012 Sivadas .............. H04N 1/00307
600/300
2014/0136450 A1 5/2014 Lee

OTHER PUBLICATIONS

Maragos et al, Measuring the Fractal Dimension of Signals: Morphological Covers and Iterative Optimization , 1993, IEEE transactions on signal processing (Year: 1993).*
av9n.clm, Introduction to Scaling Laws, 2007 (Year: 2007).*

* cited by examiner

*Primary Examiner* — Austin Hicks
(74) *Attorney, Agent, or Firm* — Procoolo. Cory, Hargreaves & Savitch LLP

(57) ABSTRACT

A mood score calculation system includes a processor and a memory. The memory is configured to hold relationship information on a relationship between a mood score of a user and a statistical feature for indicating fluctuation of operational interval time of a user terminal. The processor is configured to acquire an operation log of a first user terminal. The processor is configured to calculate, from the operation log, a value of a statistical feature for indicating fluctuation of operational interval time of the first user terminal. The processor is configured to determine a mood score of a user of the first user terminal based on the value of the statistical feature and the relationship information and output the mood score.

8 Claims, 11 Drawing Sheets

| 141 | 142 | 143 | 144 | 145 |
|---|---|---|---|---|
| EMPLOYEE TERMINAL ID | DATE | TIME | EVENT NAME | KEY TYPE |
| PC0001 | 2014/03/13 | 10:21:01.997 | KEY_DOWN | CHAR |
| PC0001 | 2014/03/13 | 10:21:01.212 | KEY_UP | CHAR |
| PC0001 | 2014/03/13 | 10:21:09.061 | KEY_DOWN | RETURN |
| PC0001 | 2014/03/13 | 10:21:09.294 | KEY_UP | RETURN |
| PC0001 | 2014/03/13 | 10:21:13.815 | L_BUTTON_DOWN | - |
| PC0001 | 2014/03/13 | 10:21:14.003 | L_BUTTON_UP | - |
| ... | ... | ... | ... | ... |

OPERATION INFORMATION 140

| 151 | 152 | 153 | 154 | 155 |
|---|---|---|---|---|
| EMPLOYEE TERMINAL ID | DATE | TIME | EVENT NAME | KEY TYPE |
| PC0001 | 2014/03/13 | 10:21:01.997 | KEY_DOWN | CHAR |
| PC0001 | 2014/03/13 | 10:21:01.212 | KEY_UP | CHAR |
| PC0001 | 2014/03/13 | 10:21:09.061 | KEY_DOWN | RETURN |
| PC0001 | 2014/03/13 | 10:21:09.294 | KEY_UP | RETURN |
| PC0001 | 2014/03/13 | 10:21:13.815 | L_BUTTON_DOWN | - |
| PC0001 | 2014/03/13 | 10:21:14.003 | L_BUTTON_UP | - |
| ... | ... | ... | ... | ... |
| PC0002 | 2014/03/13 | 10:21:13.122 | KEY_DOWN | DOWN |
| PC0002 | 2014/03/13 | 10:21:13.361 | KEY_UP | DOWN |
| PC0002 | 2014/03/13 | 10:21:14.001 | KEY_DWON | DELETE |
| PC0002 | 2014/03/13 | 10:21:14.202 | KEY_UP | DELETE |
| PC0002 | 2014/03/13 | 10:21:14.597 | KEY_DWON | RIGHT |
| PC0002 | 2014/03/13 | 10:21:14.808 | KEY_UP | RIGHT |
| ... | ... | ... | ... | ... |

OPERATIONAL TIME SERIES DATA TABLE 105

| | 181 | 182 | 183 | 184 | 185 |
|---|---|---|---|---|---|
| EMPLOYEE TERMINAL ID | DATE | TOTAL NUMBER OF TARGET EVENTS | FLUCTUATION STATISTICAL FEATURE | COEFFICIENT OF DETERMINATION |
| PC0001 | 2014/03/13 | 1273 | 0.712 | 0.9998 |
| PC0001 | 2014/03/14 | 991 | 0.709 | 0.9985 |
| PC0001 | 2014/03/17 | 2720 | 0.609 | 0.8920 |
| ... | ... | ... | ... | ... |
| PC0002 | 2014/03/13 | 3455 | 0.698 | 0.9929 |
| PC0002 | 2014/03/14 | 13 | NaN | NaN |
| PC0002 | 2014/03/17 | 1064 | 0.788 | 0.9999 |
| ... | ... | ... | ... | ... |

FLUCTUATION STATISTICAL FEATURE ANALYSIS RESULT TABLE 180

MOOD SCORE ANALYSIS RESULT TABLE 190

| EMPLOYEE TERMINAL ID (191) | DATE (192) | MOOD SCORE (193) |
|---|---|---|
| PC0001 | 2014/03/13 | 9.12 |
| PC0001 | 2014/03/14 | 9.09 |
| PC0001 | 2014/03/17 | ABNORMAL |
| ... | ... | ... |
| PC0002 | 2014/03/13 | 8.98 |
| PC0002 | 2014/03/14 | NaN |
| PC0002 | 2014/03/17 | 9.88 |
| ... | ... | ... |

MOOD SCORE CALCULATION SYSTEM

CROSS-REFERENCE TO RELATED APPLICATIONS

This application is a U.S. National Stage entry of PCT Application No. PCT/JP2015/067465, filed on Jun. 17, 2015, the contents of which are incorporated herein by reference.

BACKGROUND

This invention relates to a mood score calculation system.

Social loss due to mental illness amounts to 2 trillion yen annually in Japan alone, and is a major social problem. In particular, office workers suffer from mental illness in many cases, and establishment of methods for prevention and early detection of mental illness and efficient return to work for workers who have taken a leave of absence due to mental illness are now urgent issues. Under such circumstances, there is a demand for a technology for scientifically quantifying mental health conditions of workers.

In general, workers undergo evaluations of their working hours or moods during work as a measure to quantify conditions of workers for mental health management. Evaluation of working hours can be conducted relatively easily with a method of, for example, recording the time when a PC is turned on/off.

On the other hand, regarding evaluation of moods, moods are currently evaluated using, for example, the Profile of Mood States (POMS) or the Beck Depression Inventory-Second Edition (BDI-II). However, subjects need to answer dozens of questions each time, resulting in a heavy burden on the subjects and difficulty in conducting evaluation on an everyday basis. In view of this, a method of quantifying moods on an everyday basis without causing a burden on subjects is required.

For example, in Patent Document 1, there is disclosed an apparatus for measuring the behavior and condition of a user with various types of sensors, questioning the user about his or her mental condition, setting a combination of the answer and measurement data as learning data, and creating a model for estimating the mental condition from the learning data (for example, refer to claims).

Patent Document 1: U.S. 2014/0136450 A1

SUMMARY

In Patent Document 1, the apparatus is configured to calculate fundamental indicators such as a keyboard input speed of a terminal user and a frequency of use of a backspace key, and also configured to question the user about his or her mental condition, to thereby acquire training data for learning. Through machine learning of the training data, the mental condition of the user is determined based on a group of those indicators.

However, in some cases, the mental condition of the user is not determined significantly based on magnitudes of the group of fundamental indicators shown in Patent Document 1. Therefore, a technology for significantly estimating the mood of the terminal user based on history information on terminal operations is required.

A representative example of this invention is a mood score calculation system, including: a processor; and a memory, the memory being configured to hold relationship information on a relationship between a mood score of a user and a statistical feature for indicating fluctuation of operational interval time of a user terminal, the processor being configured to: acquire an operation log of a first user terminal; calculate, from the operation log, a value of a statistical feature for indicating fluctuation of operational interval time of the first user terminal; determine a mood score of a user of the first user terminal based on the value of the statistical feature and the relationship information; and output the mood score.

According to one embodiment of this invention, it is possible to accurately measure the mood score of a terminal user without necessitating attention of the terminal user.

DETAILED DESCRIPTION OF THE EMBODIMENTS

An embodiment of this invention is described below with reference to the accompanying drawings. It should be noted that the embodiment described below is merely an example for realizing this invention and does not limit a technical scope of this invention. Unless otherwise specified, components common across the respective drawings are denoted by the same reference symbols.

A mood measuring system of this embodiment is configured to acquire time series data on keyboard operations and mouse operations of a terminal user and analyze fluctuation of operational interval time, to thereby calculate a mood score. Specifically, the mood measuring system is configured to: acquire time series data on keyboard operations and mouse operations of the terminal user for a predetermined period of time; calculate a statistical feature for indicating the fluctuation of operational interval time for the predetermined period of time; calculate the mood score of the terminal user based on the statistical feature; and display the mood score on a terminal of an administrator.

According to the research and development conducted by the inventors of this invention, the fluctuation of operational interval time in a user terminal has relevance to the mood of the user. In particular, a fractal dimension of the operational interval time and a scaling-law index of a cumulative probability distribution of the operational interval time have high relevance to the mood score. Through calculation of the mood score of the terminal user based on the statistical feature indicating fluctuation of the operational interval time, it is possible to accurately measure the mood score of the terminal user without necessitating attention of the terminal user.

Figure 1:
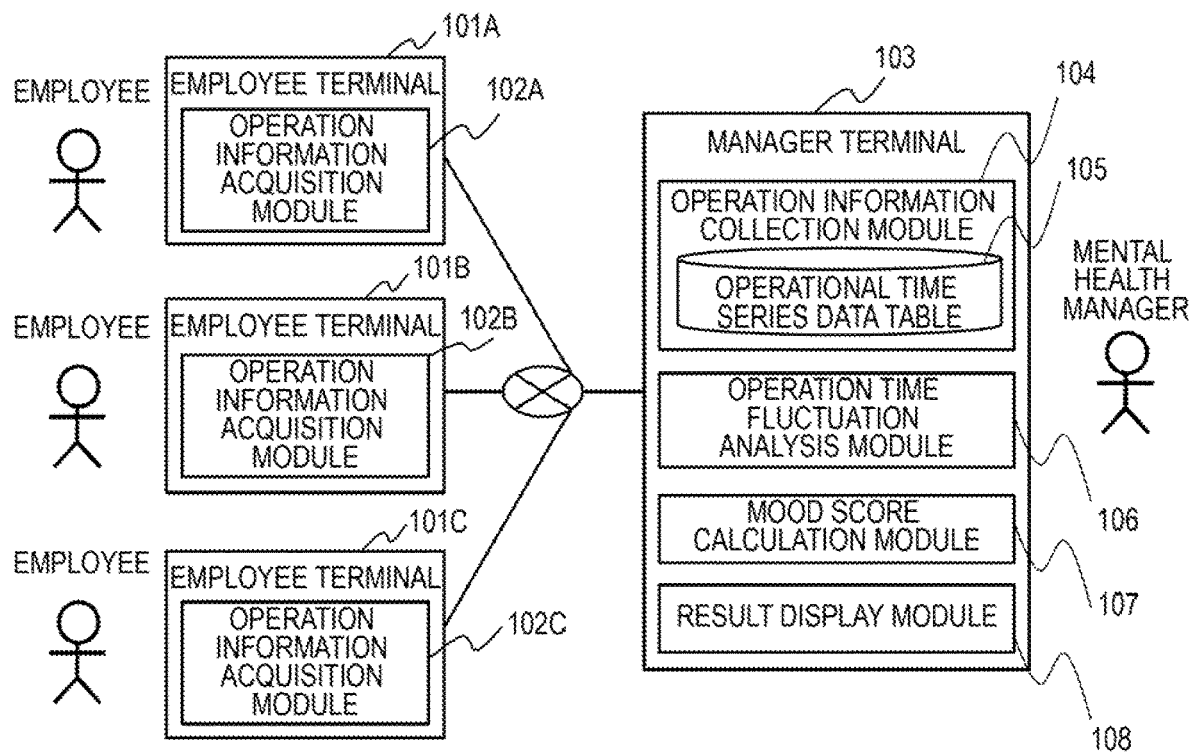
FIG. 1 is an illustration of a configuration example of the mood measuring system of this embodiment.

FIG. 1 is an illustration of a configuration example of the mood measuring system of this embodiment. The mood measuring system includes a plurality of employee terminals 101A to 101C and a manager terminal 103, which are coupled to one another via a network. Employees are users of the employee terminals 101A to 101C, respectively, and perform tasks using the employee terminals 101A to 101C. The manager terminal 103 is used by a mental health manager.

The employee terminals 101A to 101C include operation information acquisition modules 102A to 102C, respectively. The operation information acquisition modules 102A to 102C are configured to hold operation logs of the employee terminals 101A to 101C produced by the employees, respectively, and transmit the operation logs to the manager terminal 103 via the network at a predetermined timing. In the example of FIG. 1, one employee uses one employee terminal. Otherwise, the plurality of employees may use one employee terminal. Operations of respective employees are distinguished from one another by an employee ID at the time of login.

The manager terminal 103 includes an operation information collection module 104, an operation time fluctuation analysis module 106, a mood score calculation module 107, and a result display module 108. The operation information collection module 104 is configured to collect the operation logs of the employees from the employee terminals 101A to 101C at a predetermined timing via the network, and store the operation logs into an operational time series data table 105. The operation time fluctuation analysis module 106 is configured to analyze the collected operation logs of respective employees, and determine the fluctuation of the operational interval time for the operation of each employee.

The mood score calculation module 107 is configured to calculate the mood score of each employee based on the result of analysis by the operation time fluctuation analysis module 106. The result display module 108 is configured to display on a display device the mood measurement result of each employee including the mood score.

Figure 2:
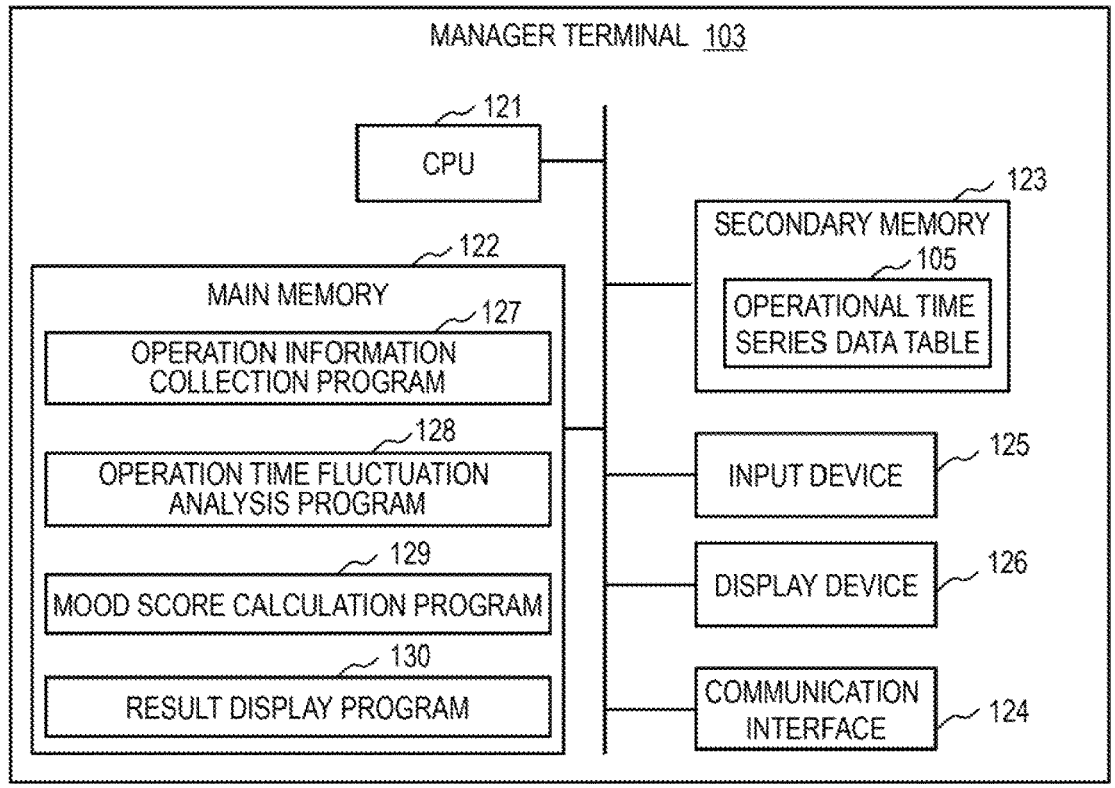
FIG. 2 is an illustration of a configuration example of the manager terminal.

FIG. 2 is an illustration of a configuration example of the manager terminal 103. The manager terminal 103 is a normal computer in terms of hardware configuration. The manager terminal 103 includes a CPU 121, a main memory 122, a secondary memory 123, a communication interface 124 configured to communicate data to/from another apparatus via a network, an input device 125, and a display device 126. The CPU 121 is a processor or arithmetic resources, while the main memory 122 and the secondary memory 123 are storage or storage resources. In this example, the manager system includes one manager terminal 103, but may include a plurality of computers.

As a representative example, the main memory 122 is a volatile semiconductor memory device. As a representative example, the secondary memory 123 is a hard disk drive (HDD) or a solid state drive (SDD), which is a non-volatile storage device including a non-transitory storage medium. An example of the input device 125 is a mouse or a keyboard, and an example of the display device 126 is a liquid crystal display.

The main memory 122 is configured to store a program and data to be used by the program. The secondary memory 123 includes a non-volatile and non-transitory storage medium configured to store a program to be loaded into the main memory 122 and data. The secondary memory 123 may be an external storage device that is coupled to the manager terminal 103 via a network. The program may be installed into an apparatus by a program distribution server or a non-transitory storage medium that can be read by a computer, and may be stored into a non-volatile storage device of each apparatus.

In FIG. 2, the main memory 122 stores an operation information collection program 127, an operation time fluctuation analysis program 128, a mood score calculation program 129, and a result display program 130 loaded from the secondary memory 123 as well as an OS (not shown). The secondary memory 123 stores the operational time series data table 105 to be loaded into the main memory 122.

A program is executed by a processor (CPU) to perform predetermined processing. Thus, when a description is given with a program as a subject in this disclosure, the subject may be the processor instead. In other cases, processing to be executed by a program is processing to be performed by an apparatus or a system that operates the program.

The processor operates as a function module for implementing a predetermined function by operating in accordance with a program. For example, the CPU 121 functions as the operation information collection module 104, the operation time fluctuation analysis module 106, the mood score calculation module 107, and the result display module 108 by operating in accordance with the operation information collection program 127, the operation time fluctuation analysis program 128, the mood score calculation program 129, and the result display program 130, respectively.

The employee terminals 101A to 101C may each have the same hardware configuration as that of the manager terminal 103. Processors of the employee terminals 101A to 101C execute operation information acquisition programs to function as the operation information acquisition modules 102A to 102C, respectively.

Figures 3, 4:
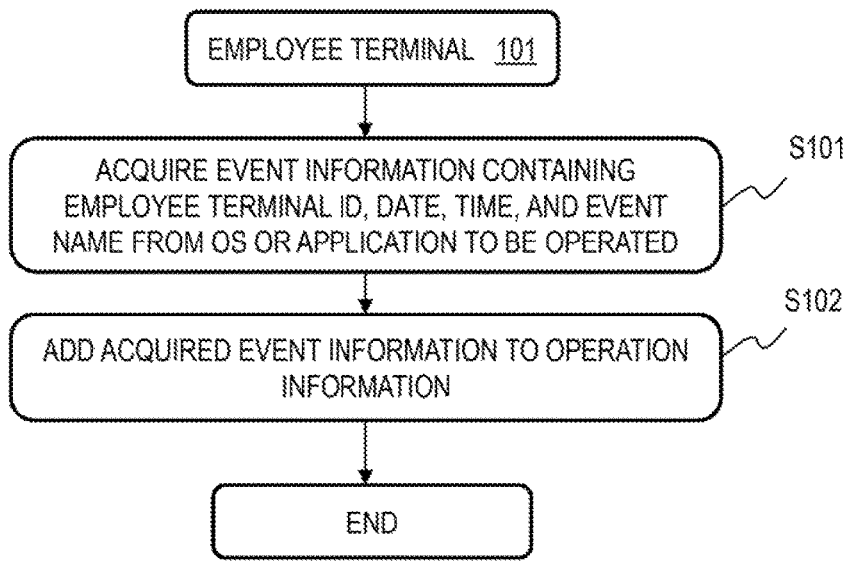
FIG. 3 is an exemplary illustration of an operation flow of the operation information acquisition module in the employee terminal.
FIG. 4 is an illustration of a configuration example of operation information to be generated by the operation information acquisition module.

FIG. 3 is an exemplary illustration of an operation flow of the operation information acquisition module 102A in the employee terminal 101A. This flow is executed each time an employee operates the employee terminal 101A to cause an event. The same applies to the other employee terminals 101B and 101C.

The operation information acquisition module 102A acquires event information containing an employee terminal ID, a date, a time, and an event name from the OS or an application to be operated (S101). The operation information acquisition module 102A adds the acquired event information to the operation information (S102). The operation information is stored in, for example, the secondary memory.

FIG. 4 is an illustration of a configuration example of operation information 140 to be generated by the operation information acquisition module 102A. An input device to be operated by an employee is, for example, a keyboard, a mouse, or a touch panel. The operation information 140 contains an employee terminal ID column 141, a date column 142, a time column 143, an event name column 144, and a key type column 145.

One record represents an event caused by an operation by the employee. One record corresponds to one operation. One operation may be formed of one or a plurality of events depending on the design. For example, key-down and key-up may each be one operation, or a combination of key-down and key-up may be one operation.

The employee terminal ID column 141 represents an ID of an operated employee terminal. The date column 142 and the time column 143 represent a date and time at which an event has occurred, respectively. The event name column 144 represents a name of the event that has occurred. The key type column 145 represents the type of an operated key when the operated input device is a keyboard or a touch panel.

Figures 5, 6:
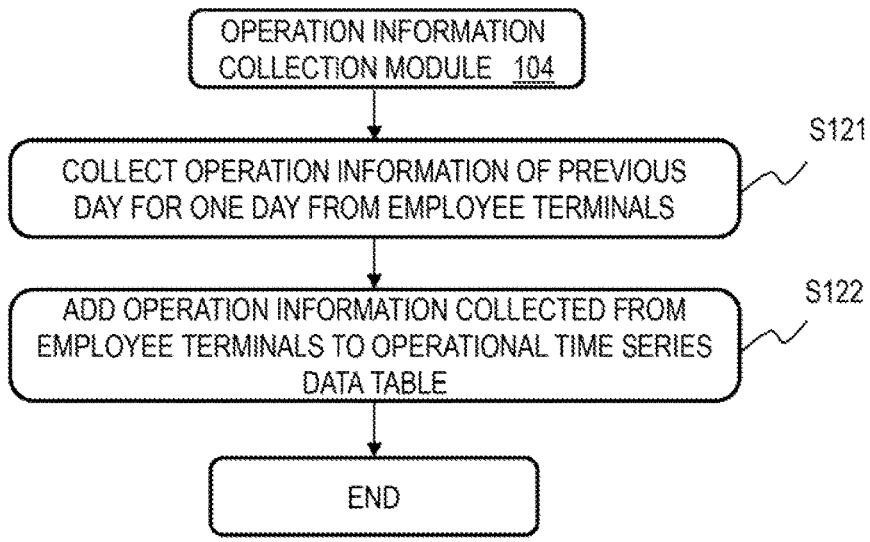
FIG. 5 is an exemplary illustration of an operation flow of the operation information collection module in the manager terminal.
FIG. 6 is an illustration of a configuration example of the operational time series data table in the manager terminal.

FIG. 5 is an exemplary illustration of an operation flow of the operation information collection module 104 in the manager terminal 103. The operation information collection module 104 collects operation information of the previous day for one day from the employee terminals 101A to 101C (S121). The operation information collection module 104 instructs each of the employee terminals 101A to 101C to transmit operation information of a specified period.

The operation information acquisition modules 102A to 102C each transmit operation information of the specified period to the manager terminal 103. The operation information collection module 104 adds the operation information collected from the employee terminals 101A to 101C to the operational time series data table 105 (S122).

FIG. 6 is an illustration of a configuration example of the operational time series data table 105 in the manager terminal 103. The operational time series data table 105 has the same table structure as that of the operation information 140. Specifically, the operational time series data table 105 contains an employee terminal ID column 151, a date column 152, a time column 153, an event name column 154, and a key type column 155.

Figure 7:
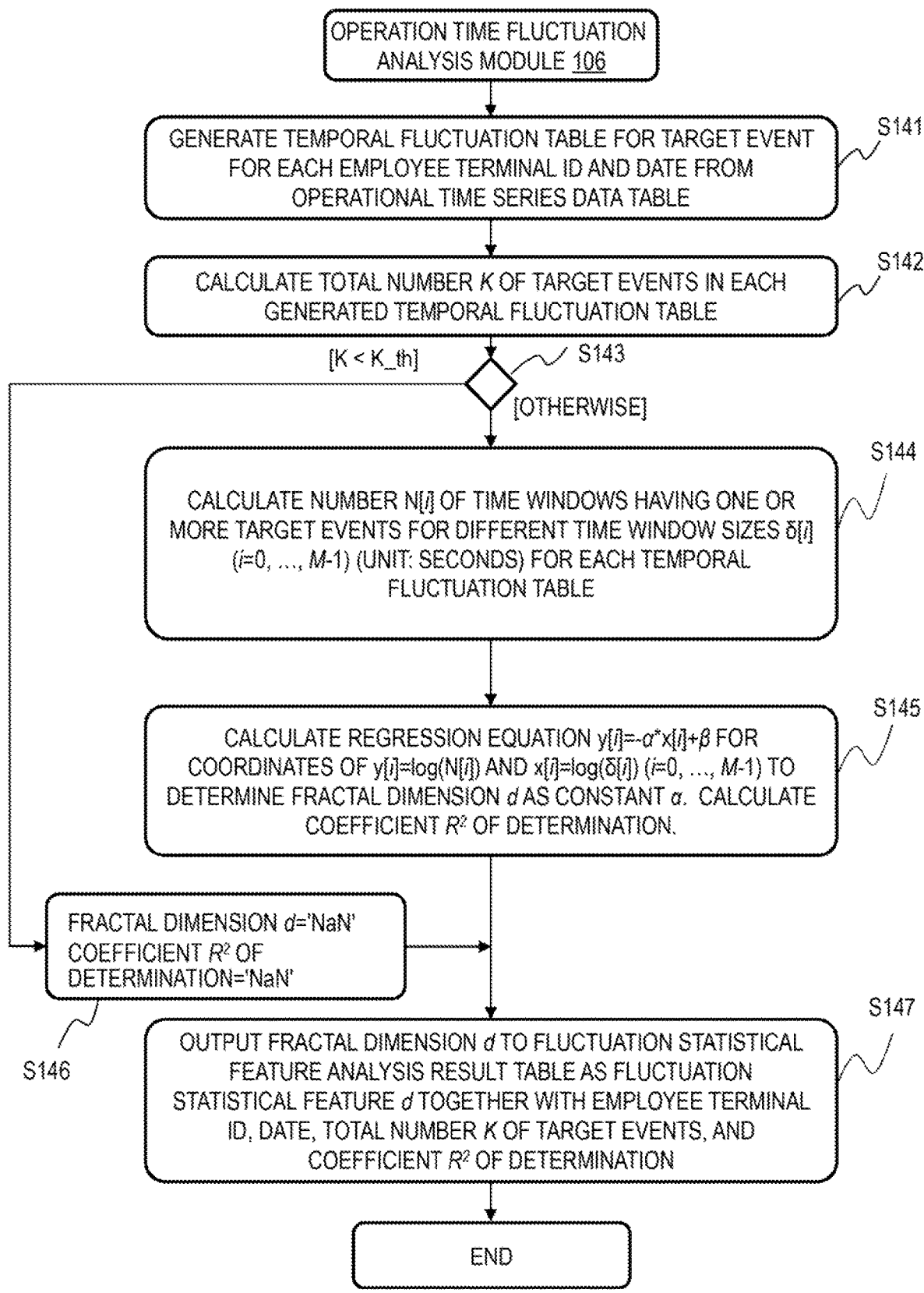
FIG. 7 is an exemplary illustration of an operation flow of the operation time fluctuation analysis module in the manager terminal.

FIG. 7 is an exemplary illustration of an operation flow of the operation time fluctuation analysis module 106 in the manager terminal 103. The operation time fluctuation analysis module 106 analyzes the operational time series data table 105 to calculate a statistical feature of fluctuation of the operational interval time for an operation performed by each of the employee terminals 101A to 101C in a predetermined period. In this example, the operation time fluctuation analysis module 106 calculates a fractal dimension of the operation time for one day as the statistical feature of fluctuation of the operational interval time for an operation performed in a predetermined period. The operational interval time is an interval time between target operations. The predetermined period is determined based on design.

FIG. 7 is an illustration of a procedure of calculating a fractal dimension d by box counting. The fractal dimension d by box counting is defined by Expression 1.

$$d = -\lim_{\delta \to 0} \frac{\log N(\delta)}{\log \delta} \qquad (1)$$

$\delta$ represents a time window size. N represents the number of time windows having one or more target events. In the following procedure, the operation time fluctuation analysis module 106 calculates the fractal dimension (d) by box counting defined in Expression 1 for each employee (employee terminal).

First, the operation time fluctuation analysis module 106 selects a record of a target event defined in advance for each employee terminal ID and date from the operational time series data table 105, and generates a temporal fluctuation table (S141). One temporal fluctuation table represents event information for one day of one employee terminal.

Figures 8, 9:
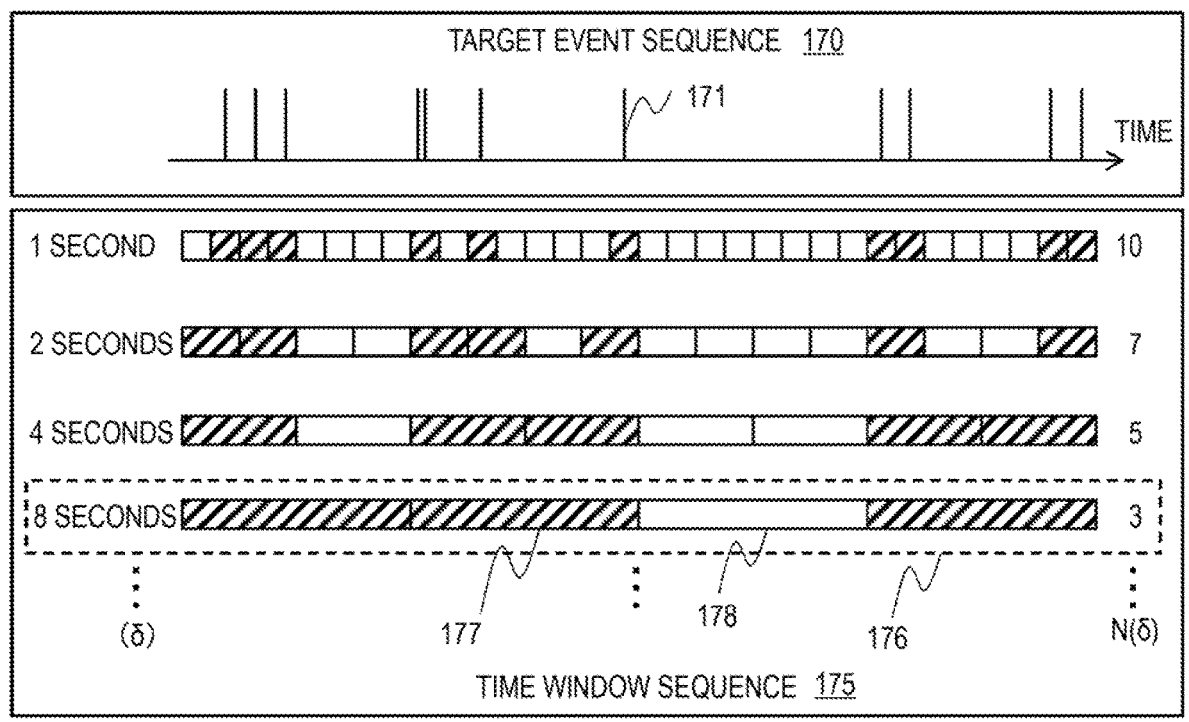
FIG. 8 is an illustration of a configuration example of a temporal fluctuation table generated by the operation time fluctuation analysis module.
FIG. 9 is an illustration of an exemplary method of calculating the number N[i] of time windows.

FIG. 8 is an illustration of a configuration example of a temporal fluctuation table 160 generated by the operation time fluctuation analysis module 106. FIG. 8 is an illustration of the temporal fluctuation table 160 extracted from the operational time series data table 105 under the condition of the employee terminal ID="PC0001", the date="2014/03/13", and the event name="KEY_DOWN". The temporal fluctuation table 160 contains a record number (#) column 161 and a time column 162. The time column 162 represents a time at which each target event occurred. The target event in this example is a key-down (key input).

In the example of FIG. 8, only information of one type of event is extracted, but the operation time fluctuation analysis module 106 may extract information of a plurality of types of events. The plurality of types of events may be events caused by the same input device, or may be events caused by different input devices. The condition for extracting events may contain conditions other than the event name.

Referring back to FIG. 7, the operation time fluctuation analysis module 106 calculates the total number K of target events in each generated temporal fluctuation table (S142). The total number K of target events is the same as the number of records of the temporal fluctuation table. In the example of FIG. 7, the total number K of target events is the number of times that key-down is performed in one day in the employee terminal.

The operation time fluctuation analysis module 106 compares the total number K of target events with a threshold value K_th (S143). When the total number K of target events is equal to or larger than the threshold value K_th (S143: otherwise), the operation time fluctuation analysis module 106 calculates the number N[i] of time windows having one or more target events for different time window sizes $\delta$[i] (i=0, . . . , M−1) (unit: seconds) (S144).

FIG. 9 is an illustration of an exemplary method of calculating the number N[i] of time windows. A section 170 represents time series data on the target event for one day in one employee terminal. One line 171 on the time axis represents one target event (key-down).

A section 175 represents time window sequences having different time window sizes $\delta$[i] (i=0, . . . , M−1). In this example, the time window size $\delta$[i] is represented by $2^i$ ((i=0, . . . , M−1)). M is a defined integer of 2 or more. The operation time fluctuation analysis module 106 calculates the number N[i] of time windows having one or more target events by changing the time window size δ[i]=2^i (i=0, ..., M−1) (unit: seconds).

For example, regarding a time window sequence 176 whose time window size is 8 seconds (δ[3]), the number N of time windows having one or more target events is three. The hatched time window (for example, time window 177) is a time window having one or more target events. A white time window (for example, time window 178) is a time window that does not have a target event. Regarding respective time window sizes other than 8 seconds, namely, 1 second, 2 seconds, and 4 seconds, the numbers N of time windows having one or more target events are 10, 7, and 5, respectively.

Referring back to FIG. 7, the operation time fluctuation analysis module 106 calculates a log-log graph (log-log relationship) of the time window size δ[i] and the number N[i] of time windows, and calculates a slope of an approximation line (S145). Specifically, the operation time fluctuation analysis module 106 calculates coordinates of y[i]=log (N[i]) and x[i]=log(δ[i]) (i=0, ..., M−1), and determines a regression equation y[i]=−α*x[i]+β.

The operation time fluctuation analysis module 106 calculates constants α and β by, for example, a least square method. The operation time fluctuation analysis module 106 determines the slope α as the fractal dimension d. Further, the operation time fluctuation analysis module 106 calculates a coefficient $R^2$ of determination, which indicates how well the regression equation fits the coordinates.

Figures 10, 11:
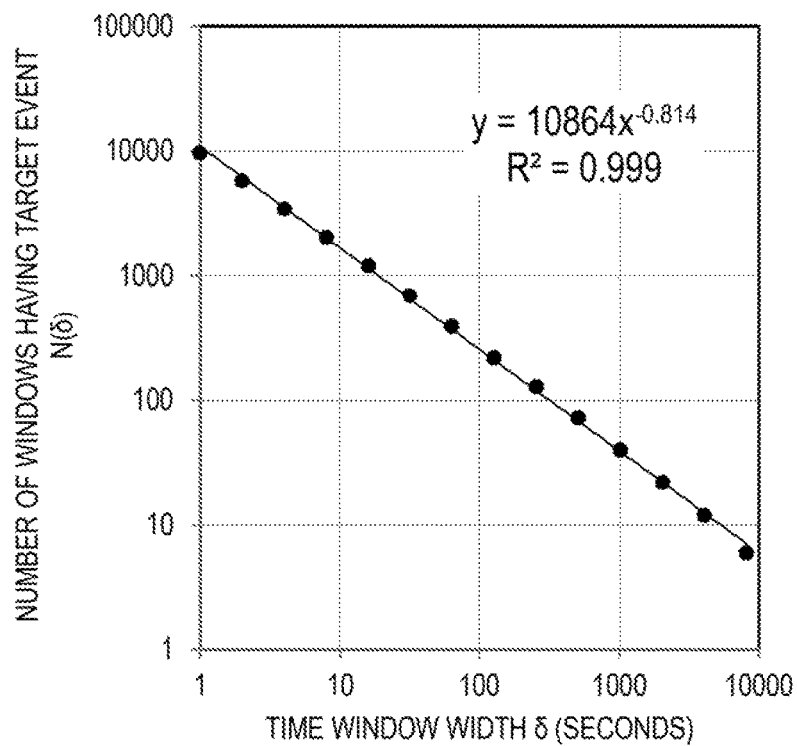
FIG. 10 is an illustration of examples of the log-log graph and the regression line for the time window size δ[i] and the number N[i] of time windows having target events.
FIG. 11 is an illustration of a configuration example of a fluctuation statistical feature analysis result table.

FIG. 10 is an illustration of examples of the log-log graph and the regression line for the time window size δ[i] and the number N[i] of time windows having target events. Points shown in FIG. 10 represent measured values, and a line represents the regression line for the measured values. The slope −α of the regression line is "−0.814", and the fractal dimension d is 0.814. Further, the coefficient $R^2$ of determination is 0.999. As can be understood from FIG. 10, the interval time for key input exhibits fractal nature with high accuracy. The inventors of this invention have conducted many measurements for the operational interval time, and have proved that the measurement result exhibits fractal nature with high accuracy.

Referring back to FIG. 7, in Step S143, when the total number K of target events is smaller than the threshold value K_th (S143: K<K_th), the operation time fluctuation analysis module 106 determines the fractal dimension d as "NaN", and further determines the coefficient $R^2$ of determination as "NaN" (S146). "NaN" is an error value indicating that the calculation result is not a normal one. When the total number K of target events is small, it is difficult to accurately calculate the fractal dimension and the mood score. Thus, a non-numeric value is presented to avoid provision of erroneous information on the moods of employees.

Lastly, the operation time fluctuation analysis module 106 outputs the fractal dimension d to a fluctuation statistical feature analysis result table as the fluctuation statistical feature d of the terminal operational interval time together with the employee terminal ID, the date, the total number K of target events, and the coefficient $R^2$ of determination (S147). The fluctuation statistical feature analysis result table is stored in the secondary memory 123.

FIG. 11 is an illustration of a configuration example of a fluctuation statistical feature analysis result table 180. The fluctuation statistical feature analysis result table 180 contains an employee terminal ID column 181, a date column 182, a total-number-of-target-events column 183, a fluctuation statistical feature column 184, and a coefficient-of-determination column 185. One record represents information on one employee terminal (one employee) for one day. As described above, the fluctuation statistical feature represents the fractal dimension d of the operational interval time.

The above-mentioned example adopts the box dimension as the fractal dimension, but another fractal dimension may be adopted. For example, the Renyi dimension, the Hausdorff dimension, the packing dimension, or the correlation dimension may be adopted.

Figure 12:
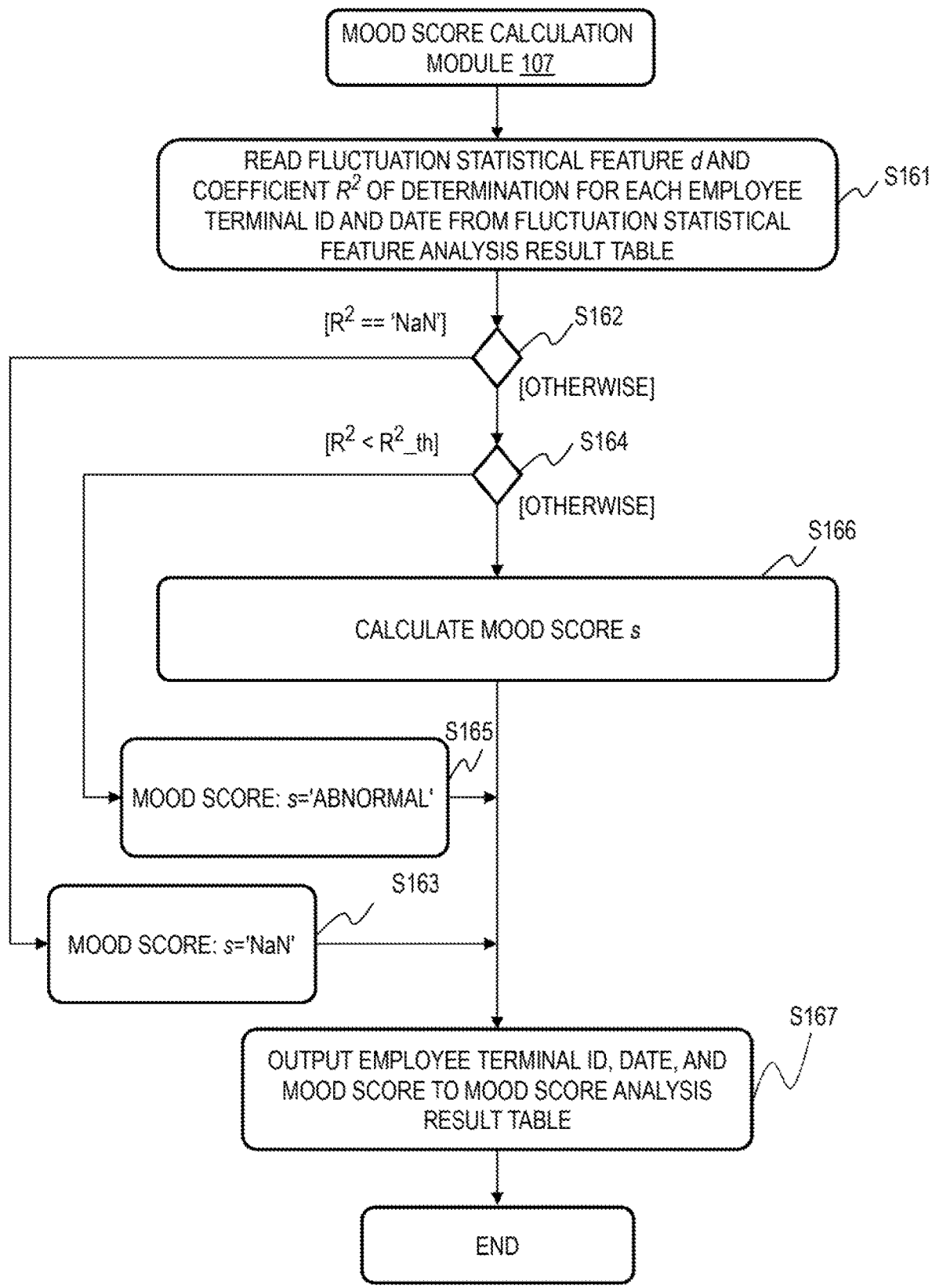
FIG. 12 is an exemplary illustration of an operation flow of the mood score calculation module.

FIG. 12 is an exemplary illustration of an operation flow of the mood score calculation module 107. The mood score calculation module 107 uses the fluctuation statistical feature calculated by the operation time fluctuation analysis module 106 to calculate the mood score of an employee.

The mood score calculation module 107 reads the fluctuation statistical feature d and the coefficient $R^2$ of determination (record) for each employee terminal ID and date from the fluctuation statistical feature analysis result table 180 (S161). One record represents information on one employee terminal for one day. The mood score calculation module 107 determines a mood score s for each employee terminal ID and day. In the following, a method of calculating the mood score of each record is described.

The mood score calculation module 107 determines whether or not the read coefficient $R^2$ of determination is "NaN" (S162). When the read coefficient $R^2$ of determination is "NaN" (S162: $R^2$==NaN), the mood score calculation module 107 determines the mood score s of the record (the date of the employee terminal ID) as "NaN" (S163). Occurrence of an error is presented to avoid provision of erroneous information on the moods of employees.

When the read coefficient $R^2$ of determination is not "NaN" (S162: otherwise), the mood score calculation module 107 compares the coefficient $R^2$ of determination with a defined threshold value $R^2$_th (S164). When the coefficient $R^2$ of determination is smaller than the threshold value $R^2$_th (S164: $R^2$<$R^2$_th), the mood score calculation module 107 determines the mood score s of the record as "abnormal" (S165).

The fact that the coefficient $R^2$ of determination is small means that the operational interval time sequence does not exhibit fractal nature. According to the research and development conducted by the inventors of this invention, the normal operational interval time sequence exhibits fractal nature, and the fractal dimension and the mood score have high relevance.

However, when the operational interval time sequence does not exhibit high fractal nature, the employee is likely to be in an unusual condition. In view of this, when the coefficient $R^2$ of determination is small, occurrence of an abnormality is presented to warn the mental health manager.

When the coefficient $R^2$ of determination is equal to or more than the threshold value $R^2$_th (S164: otherwise), the mood score calculation module 107 calculates the mood score s of the record in accordance with a predetermined expression (S166). Expression 2 is shown as an example of the expression for calculating the mood score s.

$$s = a_1 d + a_2 \qquad (2)$$

a1 and a2 are constant coefficients given in advance. Expression 2 is relationship information on a relationship between the statistical feature d and the mood score. Expression 2 calculates a mood score for one type of mood, for example, anger or concern. When a plurality of types of mood scores are calculated, a plurality of combinations of a1 and a2 are given in advance. The mood score calculation module 107 uses combinations of a1 and a2 to calculate different types of mood scores in accordance with Expression 2.

a1 and a2 are determined in advance by experiment on subjects. For example, a system designer can compare the fractal dimension calculated from the operation log of a subject with the mood score of the subject determined through use of, for example, the profile of mood state (POMS) or the beck depression inventory second edition (BDI-II) to determine the coefficients a1 and a2. a1 and a2 may be common to all the employees or may be prepared for each employee.

Figures 13, 14:
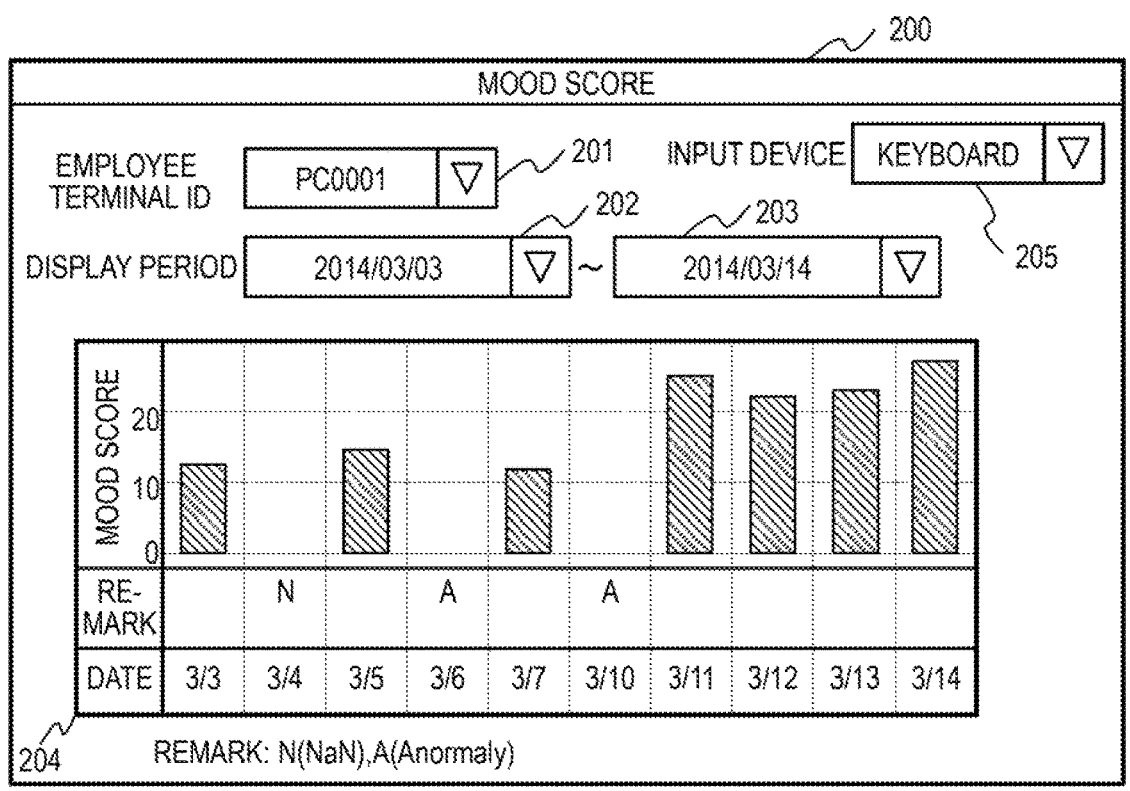
FIG. 13 is an illustration of a configuration example of a mood score analysis result table.
FIG. 14 is an illustration of an example of a mood score analysis result image.

The mood score calculation module 107 outputs the employee terminal ID, the date, and the calculated mood score to the mood score analysis result table (S167). FIG. 13 is an illustration of a configuration example of a mood score analysis result table 190. The mood score analysis result table 190 contains an employee terminal ID column 191, a date column 192, and a calculated mood score column 193. In this example, one type of mood score is calculated for a one-day operation of one employee terminal.

In the example described with reference to FIG. 7 to FIG. 13, the temporal fluctuation table 160 is created for keydown on a keyboard, and the fluctuation statistical feature (fractal dimension) and the mood score are calculated from the temporal fluctuation table 160. The manager terminal 103 may create a temporal fluctuation table for each of different operation events, and calculate the fluctuation statistical feature and the mood score from each of the temporal fluctuation tables.

For example, the operation time fluctuation analysis module 106 creates a temporal fluctuation table for indicating the interval time for a keyboard operation (for example, keydown of an arbitrary key), a temporal fluctuation table for indicating the interval time for a mouse operation (for example, button-down of an arbitrary button), and a temporal fluctuation table for indicating the interval time for both of the keyboard operation and the mouse operation.

The operation time fluctuation analysis module 106 calculates the fractal dimension and the coefficient of determination for each of the temporal fluctuation tables based on the flow described with reference to FIG. 7, and generates a fluctuation statistical feature analysis result table for each of the temporal fluctuation tables.

The mood score calculation module 107 calculates the mood score from each of the generated fluctuation statistical feature analysis result tables based on the flow described with reference to FIG. 12, and generates a mood score analysis result table. A group of constants for calculating the mood score are prepared in advance for each of the fluctuation statistical feature analysis result tables. In this manner, through calculation of a mood score for each of operations of different operation events, the mental health manager can analyze the conditions of employees more accurately.

FIG. 14 is an illustration of an example of a mood score analysis result image 200. The result display module 108 generates mood score analysis result image data from the mood score analysis result table 190 and displays the mood score analysis result image 200 using the display device 126.

The mood score analysis result image 200 contains a field 201 for selecting an employee terminal ID, fields 202 and 203 for inputting start and end of a display period, respectively, and a field 205 for inputting an input device of the operation log used for calculation of the mood score. Further, the mood score analysis result image 200 contains a section 204 in which the mood score is calculated.

The mental health manager uses the input device 125 of the manager terminal 103 to select an employee terminal ID for which information on the mood score is displayed in the field 201, and inputs a period for displaying information on the mood score in the fields 202 and 203. The mental health manager selects, in the field 205, an input device of the operation log used for calculation of the mood score. For example, any one of a keyboard, a mouse, and a keyboard and mouse may be selected.

The result display module 108 selects the mood score analysis result table 190 in accordance with the user input, and selects requested data from the selected mood score analysis result table 190. The result display module 108 generates image data of the section 204 for displaying the mood score and outputs the image data to the display device 126.

The section 204 represents the mood score in each day of a designated period of a designated employee terminal. The mood score is a value calculated from the operation log of a designated input device. The section 204 may represent information on the fluctuation statistical feature or information on the coefficient of determination in addition to information on the mood score.

Figure 15:
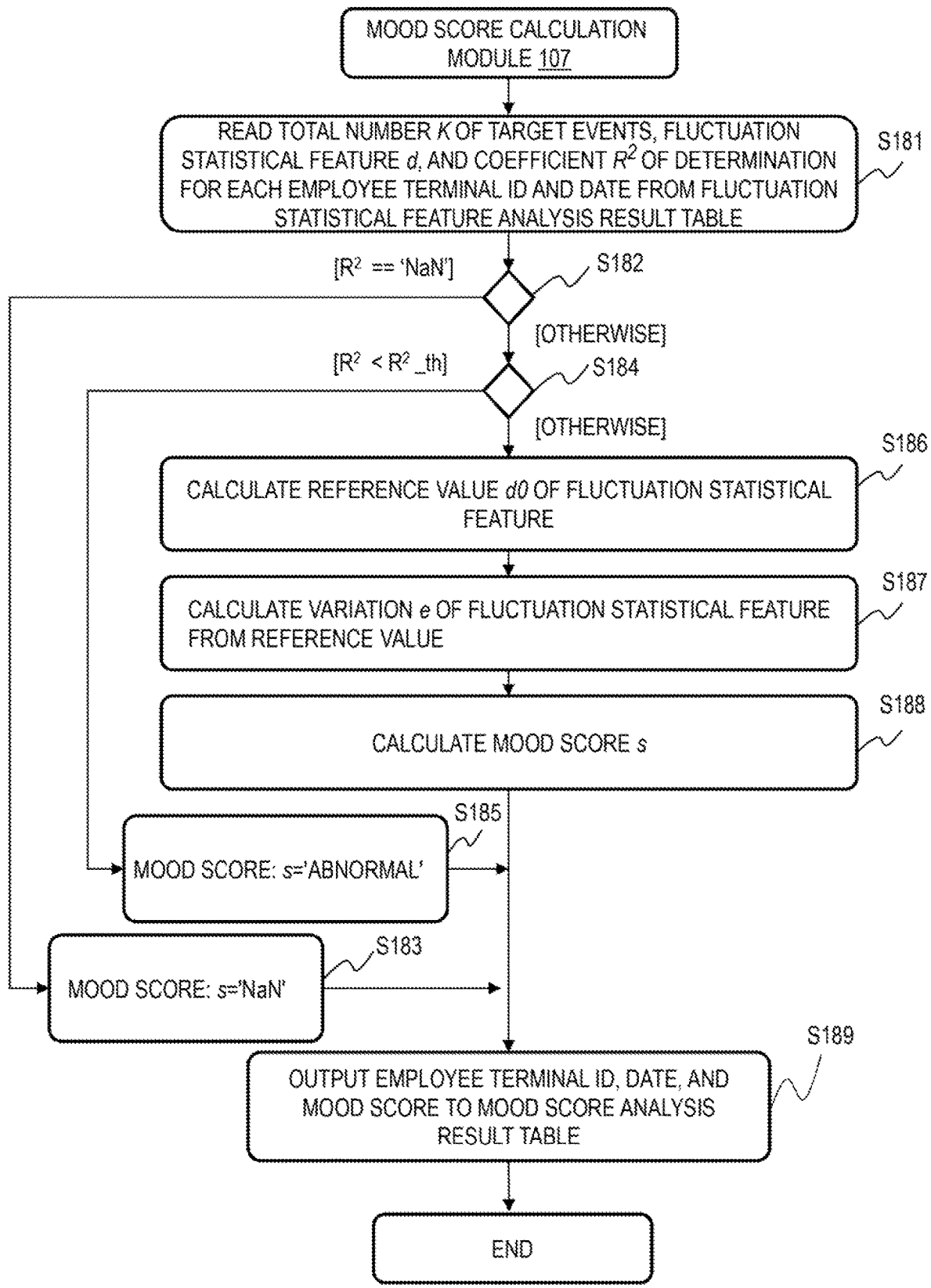
FIG. 15 is an illustration of another example of a method of calculating a mood score by the mood score calculation module.

FIG. 15 is an illustration of another example of a method of calculating a mood score by the mood score calculation module 107. In this example, the mood score calculation module 107 uses the total number K of target events to calculate a reference value of the statistical feature of fluctuation, and calculates the mood score based on the reference value and the statistical feature of fluctuation calculated by the operation time fluctuation analysis module 106. In the following, a description is mainly given of a difference from the mood score calculation operation illustrated in FIG. 12.

According to the research and development conducted by the inventors of this invention, as the total number K of target events increases, the fractal dimension also tends to increase. In other words, when an employee is busy, the fractal dimension tends to be large regardless of his or her mood. In view of this, in this example, the mood score calculation module 107 subtracts components due to busyness from the fractal dimension value, to thereby calculate the fractal dimension and the mood score that match the mood of the employee more accurately.

The mood score calculation module 107 reads the fluctuation statistical feature d, the total number K of target events, and the coefficient $R^2$ of determination (record) for each employee terminal ID and date from the fluctuation statistical feature analysis result table 180 (S181). Steps S182 to S185 after Step S181 are similar to Steps S162 to S165 of FIG. 12.

In Step S186, the mood score calculation module 107 calculates a reference value d0 of the fluctuation statistical feature using the total number K of target events in accordance with a predetermined expression. Expression 3 is shown as an example of the expression for calculating the reference value d0 of the fluctuation statistical feature.

$$d_0 = b_1 + b_2 \log K \tag{3}$$

b1 and b2 are constant coefficients given in advance. b1 and b2 can be determined by experiment on subjects. Expression 3 is information on a relationship between the total number K of target events and the reference value d0.

Next, the mood score calculation module 107 calculates a variation e of the fluctuation statistical feature d from the reference value d0 (S187). Expression 4 is shown as an example of the expression for calculating the variation e.

$$e = \frac{d}{d_0} - 1 \quad (4)$$

Next, the mood score calculation module 107 calculates the mood score s based on the variation e of the fluctuation statistical feature d from the reference value d0 (S188). Expression 5 is shown as an example of the expression for calculating the mood score s.

$$s = c_1 e + c_2 \quad (5)$$

c1 and c2 are constant coefficients given in advance. c1 and c2 can be determined by experiment on subjects. Expression 5 is information on a relationship between the variation and the mood score, and Expressions 3, 4, and 5 represent relationships between the statistical feature d and the mood score s. Expression 5 calculates the mood score for one type of mood. When a plurality of types of mood scores are calculated, a plurality of combinations of c1 and c2 are given in advance. Lastly, the mood score calculation module 107 outputs the employee terminal ID, the date, and the calculated mood score to the mood score analysis result table (S189).

Figure 16:
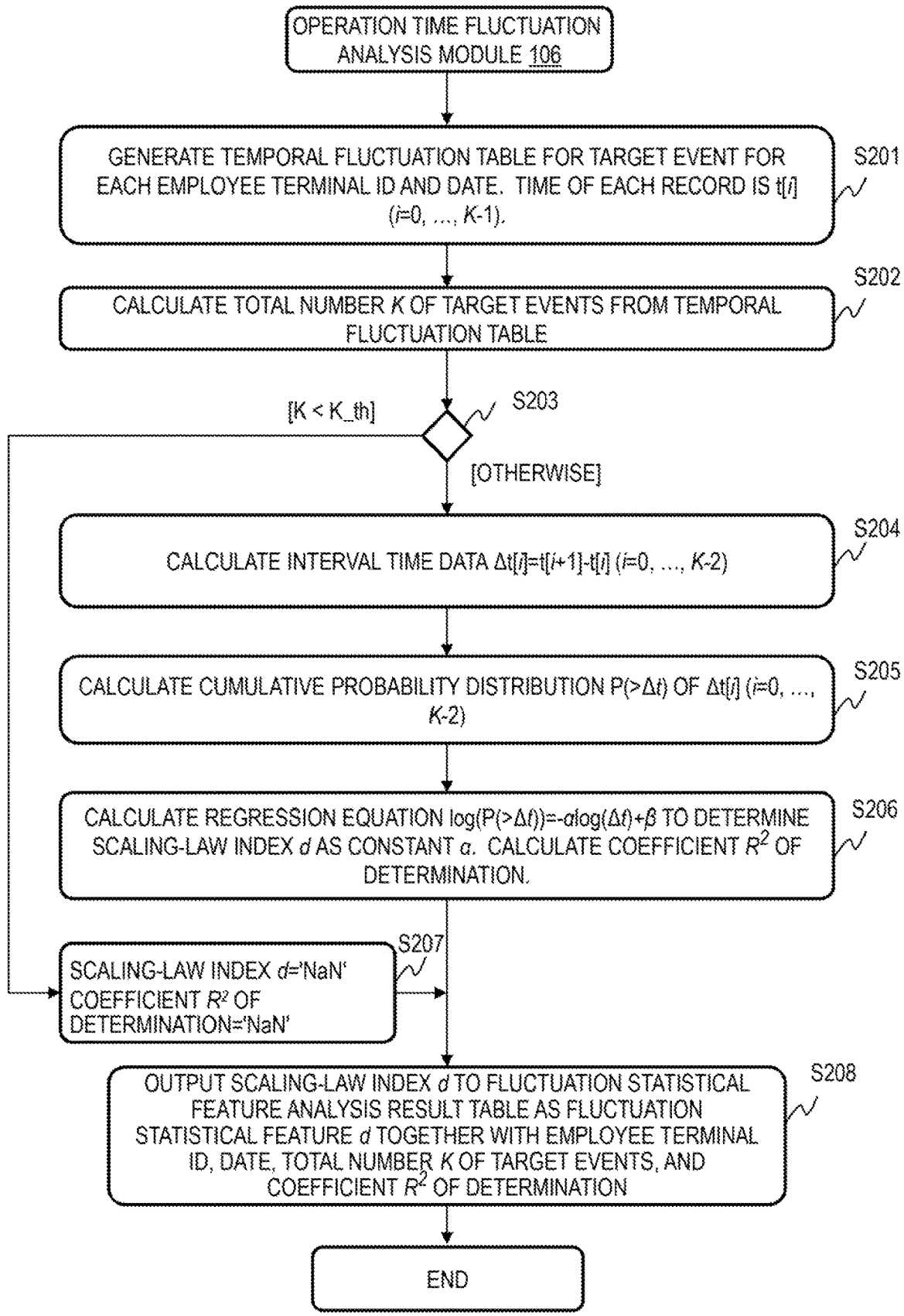
FIG. 16 is an illustration of another example of a method of calculating a fluctuation statistical feature by the operation time fluctuation analysis module.

FIG. 16 is an illustration of another example of a method of calculating a fluctuation statistical feature by the operation time fluctuation analysis module 106. In this example, the operation time fluctuation analysis module 106 assumes, as the fluctuation statistical feature, that the cumulative probability distribution of the operational interval time follows the scaling-law distribution $P(x > \Delta t) \sim (\Delta t)^{-\alpha}$, and calculates the scaling-law index $\alpha$. In this manner, a more appropriate mood score can be calculated.

First, the operation time fluctuation analysis module 106 generates a temporal fluctuation table for a target event for each employee terminal ID and date from the operational time series data table 105 (S201). The time of each record of the temporal fluctuation table is defined as t[i] (i=0, ..., K−1).

Figure 17:
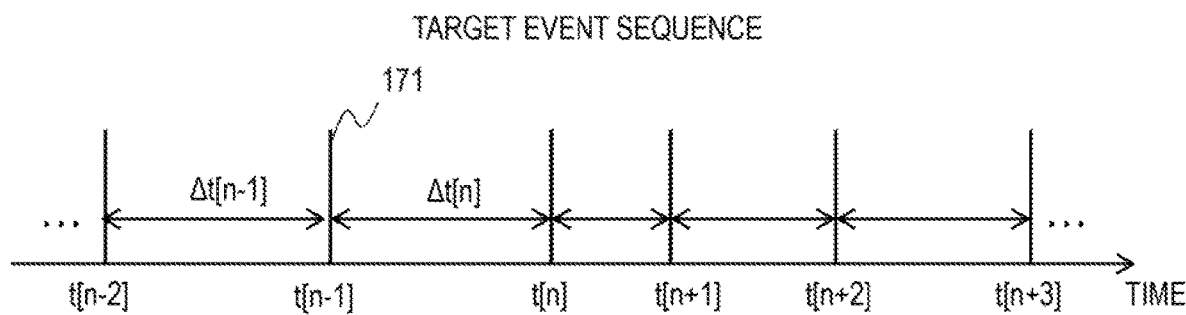
FIG. 17 is an illustration of time series data on a target event for one day in one employee terminal.

FIG. 17 is an illustration of time series data on a target event for one day in one employee terminal. One line 171 on the time axis represents one target event (key-down). The occurrence time of each event is represented by t[i]. The interval time between the event at an occurrence time t[n−1] and the event at an occurrence time t[n] is represented by $\Delta t[n]$.

Referring back to FIG. 16, the operation time fluctuation analysis module 106 calculates the total number K of target events from each of the temporal fluctuation tables 160 (S202). The total number K of target events of the temporal fluctuation table 160 is the number of records of the temporal fluctuation table 160.

In the following, the operation time fluctuation analysis module 106 executes Steps S203 to S207 for each temporal fluctuation table. The operation time fluctuation analysis module 106 compares the total number K of target events with the threshold value K_th for the temporal fluctuation table (S203).

When the total number K of target events is equal to or more than the threshold value K_th (S203: otherwise), the operation time fluctuation analysis module 106 calculates interval time data $\Delta t[i] = t[i+1] - t[i]$ (i=0, ..., K−2) (S204). The interval time data $\Delta t[i]$ indicates the interval time between successive events.

Next, the operation time fluctuation analysis module 106 calculates the cumulative probability distribution $P(>\Delta t)$ of $\Delta t[i]$ (i=0, ..., K−2) (S205). Further, the operation time fluctuation analysis module 106 calculates the log-log graph (log-log relationship) of the interval time $\Delta t$ and the cumulative probability distribution $P(>\Delta t)$, and calculates the slope of an approximation line (S206). In other words, the operation time fluctuation analysis module 106 calculates coordinates of $y[i] = P(>\Delta t[i])$ and $x[i] = \Delta t[i]$ (i=0, ..., K−2), and determines a regression equation $\log(y) = -\alpha \log(x) + \beta$.

The operation time fluctuation analysis module 106 calculates constants $\alpha$ and $\beta$ by, for example, a least square method. The operation time fluctuation analysis module 106 determines the slope $\alpha$ as the scaling-law index d. Further, the operation time fluctuation analysis module 106 calculates the coefficient $R^2$ of determination, which indicates how well the regression equation fits the coordinates.

Figure 18:
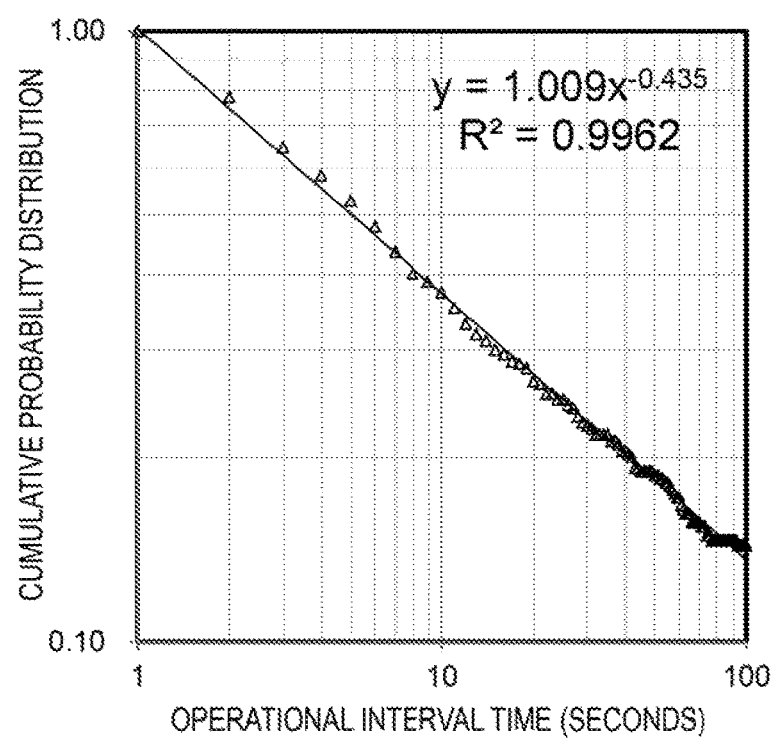
FIG. 18 is an illustration of examples of the log-log graph and the regression line for the interval time Δt and the cumulative probability distribution P(>Δt).

FIG. 18 is an illustration of examples of the log-log graph and the regression line for the interval time $\Delta t$ and the cumulative probability distribution $P(>\Delta t)$. Measured values are shown in FIG. 18. The slope $-\alpha$ of the regression line is "−0.435", and the scaling-law index d is 0.435. Further, the coefficient $R^2$ of determination is 0.9962. As can be understood from FIG. 18, the interval time of key input follows the scaling-law with high accuracy. The inventors of this invention have conducted many measurements for the operational interval time, and have proved that the measurement result exhibits scaling-law with high accuracy.

Referring back to FIG. 16, in Step S203, when the total number K of target events is smaller than the threshold value K_th (S203: K<K_th), the operation time fluctuation analysis module 106 determines the scaling-law index d as "NaN", and further determines the coefficient $R^2$ of determination as "NaN" (S207).

Lastly, the operation time fluctuation analysis module 106 outputs the scaling-law index d to the fluctuation statistical feature analysis result table as the fluctuation statistical feature d of the terminal operational interval time together with the employee terminal ID, the date, the total number K of target events, and the coefficient $R^2$ of determination (S208). The fluctuation statistical feature d calculated with reference to the flowchart of FIG. 16 is used to calculate the mood score by the method described with reference to FIG. 12 or FIG. 15.

This invention is not limited to the above-described embodiments but includes various modifications. The above-described embodiments are explained in details for better understanding of this invention and are not limited to those including all the configurations described above. A part of the configuration of one embodiment may be replaced with that of another embodiment; the configuration of one embodiment may be incorporated to the configuration of another embodiment. A part of the configuration of each embodiment may be added, deleted, or replaced by that of a different configuration.

The above-described configurations, functions, and processors, for all or a part of them, may be implemented by hardware: for example, by designing an integrated circuit. The above-described configurations and functions may be implemented by software, which means that a processor interprets and executes programs providing the functions. The information of programs, tables, and files to implement the functions may be stored in a storage device such as a memory, a hard disk drive, or an SSD (Solid State Drive), or a storage medium such as an IC card, or an SD card.

The drawings shows control lines and information lines as considered necessary for explanations but do not show all control lines or information lines in the products. It can be considered that almost of all components are actually interconnected.

What is claimed is:

1. A mood score calculation system, comprising:
a processor; and
a memory,
the memory being configured to hold relationship information on a relationship between a mood score of a user and a statistical feature for indicating fluctuation of operational interval time of a user terminal,
the processor being configured to:
acquire an operation log of a first user terminal;
calculate, from the operation log, a value of a statistical feature for indicating fluctuation of operational interval time of the first user terminal;
determine a mood score of a user of the first user terminal based on the value of the statistical feature and the relationship information; and
output the mood score,
wherein the statistical feature comprises a scaling-law index for characterizing a cumulative probability distribution of the operational interval time of the user terminal.

2. The mood score calculation system according to claim 1, wherein the statistical feature comprises a fractal dimension for characterizing the operational interval time of the user terminal.

3. The mood score calculation system according to claim 1, wherein the processor is configured to determine the mood score as an error value when a total number of operations, based on which the value of the statistical feature exhibited by the operation log is calculated, is smaller than a threshold value.

4. A mood score calculation system, comprising:
a processor; and
a memory,
the memory being configured to hold relationship information on a relationship between a mood score of a user and a statistical feature for indicating fluctuation of operational interval time of a user terminal,
the processor being configured to:
acquire an operation log of a first user terminal;
calculate, from the operation log, a value of a statistical feature for indicating fluctuation of operational interval time of the first user terminal;
determine a mood score of a user of the first user terminal based on the value of the statistical feature and the relationship information; and
output the mood score,
wherein the statistical feature comprises a fractal dimension for characterizing the operational interval time of the user terminal, and
wherein the processor is configured to:
calculate a coefficient of determination between the operation log and an approximation equation used for calculating the fractal dimension;
compare the coefficient of determination with a threshold value; and
determine the mood score as an abnormal value when the coefficient of determination is smaller than the threshold value.

5. The mood score calculation system according to claim 1, wherein the processor is configured to:
calculate a coefficient of determination between the operation log and an approximation equation used for calculating the scaling-law index;
compare the coefficient of determination with a threshold value; and
determine the mood score as an abnormal value when the coefficient of determination is smaller than the threshold value.

6. The mood score calculation system according to claim 1,
wherein the relationship information indicates a relationship between a variation of the calculated statistical feature from a reference value and the mood score, and
wherein the processor is configured to:
calculate the reference value using a number of operations in the operation log; and
determine the mood score based on the variation of the calculated statistical feature from the calculated reference value and the relationship information.

7. The mood score calculation system according to claim 1,
wherein the operation log comprises an operation log of a first input device and an operation log of a second input device, and
wherein the processor is configured to:
determine a first mood score from the operation log of the first input device and a second mood score from the operation log of the second input device; and
output the first mood score and the second mood score.

8. A method of determining a mood score, which is performed by a computer system configured to hold relationship information on a relationship between a mood score of a user and a statistical feature for indicating fluctuation of operational interval time of a user terminal, the method comprising:
acquiring, by the computer system, an operation log of a first user terminal;
calculating, by the computer system, from the operation log, a value of a statistical feature for indicating fluctuation of operational interval time of the first user terminal;
determining, by the computer system, a mood score of a user of the first user terminal based on the value of the statistical feature and the relationship information; and
outputting, by the computer system, the mood score,
wherein the statistical feature comprises a scaling-law index for characterizing a cumulative probability distribution of the operational interval time of the user terminal.

* * * * *